United States Patent
Schipper (10) Patent No.: US 9,668,698 B2
(45) Date of Patent: Jun. 6, 2017

(54) MONITORING DEVICE AND METHOD FOR COMPENSATING NON-LINEARITY EFFECTS IN VITAL SIGNS MONITORING

(71) Applicant: KONINKLIJKE PHILIPS N.V., Eindhoven (NL)

(72) Inventor: Alphonsus Tarcisius Jozef Maria Schipper, Strampoy (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/036,290

(22) PCT Filed: Mar. 26, 2015

(86) PCT No.: PCT/EP2015/056483
§ 371 (c)(1),
(2) Date: May 12, 2016

(87) PCT Pub. No.: WO2015/150200
PCT Pub. Date: Oct. 8, 2015

(65) Prior Publication Data
US 2017/0014081 A1    Jan. 19, 2017

(30) Foreign Application Priority Data

Apr. 3, 2014 (EP) ..................................... 14163298

(51) Int. Cl.
*A61B 5/00* (2006.01)
*A61B 5/024* (2006.01)
(Continued)

(52) U.S. Cl.
CPC ........ *A61B 5/7203* (2013.01); *A61B 5/02416* (2013.01); *A61B 5/0816* (2013.01);
(Continued)

(58) Field of Classification Search
CPC ........ A61B 2560/0223; A61B 5/02416; A61B 5/0816; A61B 5/14551; A61B 5/681;
(Continued)

(56) References Cited

U.S. PATENT DOCUMENTS 5,795,300 A    8/1998    Bryars
5,954,644 A    9/1999    Dettlilng et al.
(Continued)

FOREIGN PATENT DOCUMENTS

WO    2013190423 A1    12/2013

OTHER PUBLICATIONS

Neokosmidis, et al., "Impact of nonlinear LED transfer function on discrete multitone modulation; analytical approach", 2009, pp. 1-9.

*Primary Examiner* — Ruth S Smith (57) ABSTRACT

The present invention relates to a monitoring device (10) comprising a light source (14) for emitting light into a body part (12) of a living being; a light sensor (18) for receiving light (16) including an ambient light component (30) and a measurement light component (32) resulting from interactions of said emitted light with said body part (12) and for generating an output signal (34), wherein a transfer function describes the relation between the output signal (34) and the received light; an ambient light cancellation unit (20) for separating the output signal (34) into a first signal portion (36) corresponding to the ambient light component (30) and a second signal portion (38) corresponding to the measurement light component (32); and an ambient light modulation removal unit (22) for compensating a variation of the ambient light component (30) by demodulating the second signal portion (38) based on the transfer function (f) and the first signal portion (36) to generate a measurement signal (40).

15 Claims, 4 Drawing Sheets

(51) Int. Cl.
*A61B 5/1455* (2006.01)
*A61B 5/08* (2006.01)

(52) U.S. Cl.
CPC .......... *A61B 5/14551* (2013.01); *A61B 5/681* (2013.01); *A61B 5/6826* (2013.01); *A61B 5/725* (2013.01); *A61B 5/7214* (2013.01); *A61B 5/7228* (2013.01); *A61B 5/7278* (2013.01); *A61B 2560/0223* (2013.01)

(58) Field of Classification Search
CPC ... A61B 5/6826; A61B 5/7203; A61B 5/7214; A61B 5/7228; A61B 5/725; A61B 5/7278
See application file for complete search history.

(56) References Cited

U.S. PATENT DOCUMENTS

| | | |
|---|---|---|
| 5,995,858 A | 11/1999 | Kinast |
| 8,046,041 B2 | 10/2011 | Diab et al. |
| 2009/0154573 A1 | 6/2009 | Petersen |
| 2011/0137181 A1 | 6/2011 | Lin et al. |

MONITORING DEVICE AND METHOD FOR COMPENSATING NON-LINEARITY EFFECTS IN VITAL SIGNS MONITORING

CROSS-REFERENCE TO PRIOR APPLICATIONS

This application is the U.S. National Phase application under 35 U.S.C. §371 of International Application No. PCT/EP2015/056483, filed on Mar. 26, 2015, which claims the benefit of European Patent Application No. 14163298.4 filed on Apr. 3, 2014. These applications are hereby incorporated by reference herein, for all purposes.

FIELD OF THE INVENTION

The present invention relates to a monitoring device and a monitoring method as well as to an apparatus for monitoring a vital sign of a living being including the monitoring device.

BACKGROUND OF THE INVENTION

Vital signs of a person, for example the heart rate (HR), the respiration rate (RR) or the blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmissivity and/or reflectivity at different wavelengths (typically red and infrared), the blood oxygen saturation can be determined.

A typical pulse oximeter for measuring the heart rate and the (arterial) blood oxygen saturation of a subject comprises a red LED and an infrared LED as light sources and one photodiode for detecting light that has been transmitted through a body pare of a patient (i.e. through tissue comprised in a body part). Commercially available pulse oximeters quickly switch between measurements at red and an infrared wavelength and thereby measure the transmissivity of the same area or volume of tissue at two different wavelengths. This is referred to as time-division-multiplexing. The transmissivity over time at each wavelength gives the PPG waveforms for red and infrared wavelengths.

One problem with PPG is that ambient light can leak into the sensor and disturb the measurement. This ambient light may originate from the sun or from electrical lamps (which may emit light at the net frequency). Another problem is that noise, especially low frequent noise (e.g. 1/f noise), but also high frequent noise, disturbs the measurement as well. Furthermore, electromagnetic interference may disturb the measurement as well.

In WO 2013/0190423 A1, a photoplethysmographic device and method is disclosed. The disclosed device comprises a light source for emitting light pulses into tissue of a living being, a light sensor for receiving light from said tissue and generating a sensor signal, a filter unit for filtering said sensor signal, said filter unit comprising a switched in-phase low-pass filter for generating an in-phase filter signal and a switched out-of-phase low-pass filter for generating an out-of-phase filter signal, a control unit for controlling said light source and said filter unit such that the in-phase filter is only switched on during a second time period while the light source is switched on and that the out-of-phase filter is switched on during a first and third time period while the light source is switched off, a subtraction unit for subtracting the out-of-phase filter signal from the in-phase filter signal.

However, there is still room for improvements in the area of PPG vital sign detection and vital sign monitoring, in particular with respect to accuracy and reliability, especially if ambient light levels become higher (e.g. due to narrower wrist straps in case of wristwatch device) and/or if LED levels become lower in order to save power.

SUMMARY OF THE INVENTION

It is an object of the present invention to provide a monitoring device and a monitoring method that further improve the handling of potentially disturbing ambient light effects. It is further an object of the present invention to provide an apparatus for monitoring a vital sign of a living being.

In a first aspect of the present invention a monitoring device is presented comprising:
a light source for emitting light into a body part of a living being;
a light sensor for receiving light including an ambient light component and a measurement light component resulting from interactions of said emitted light with said body part and for generating an output signal, wherein a transfer function describes the relation between the output signal and the received light;
an ambient light cancellation unit for separating the output signal into a first signal portion corresponding to the ambient light component and a second signal portion corresponding to the measurement light component; and
an ambient light modulation removal unit for compensating a variation of the ambient light component by demodulating the second signal portion based on the transfer function and the first signal portion to generate a measurement signal.

In a further aspect of the present invention a corresponding monitoring method is presented comprising the steps of:
emitting light into a body part of a living being;
receiving light including an ambient light component and a measurement light component resulting from interactions of said emitted light with said body part and for generating an output signal, wherein a transfer function describes the relation between the output signal and the received light;
separating the output signal into a first signal portion corresponding to the ambient light component and a second signal portion corresponding to the measurement light component; and compensating a variation of the ambient light component by demodulating the second signal portion based on the transfer function and the first signal portion to generate a measurement signal.

In yet another aspect of the present invention an apparatus for monitoring a vital sign of a living being is presented, the apparatus comprising:

a monitoring device as disclosed herein; and a processing unit for deriving information on a vital sign of the living being from the measurement signal.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, apparatus, computer program and medium have similar and/or identical preferred embodiments as the claimed device and as defined in the dependent claims.

The present invention aims at improving the compensation of ambient light effects and variations in the level of ambient light on a measurement signal. Various monitoring devices, e.g. PPG devices, rely on the evaluation of interactions of light with a body part (i.e. tissue or blood in a body part) of a living being. For this, a light source emits light into a body part of the living being and a light sensor captures light after it has interacted with that body part. Thereby, it is either possible that a reflective measurement is carried out, i.e. light is evaluated after being reflected at the body part, or a transmissive measurement is carried out, i.e. light is evaluated after being transmitted through the body part.

It is often difficult to assure a light tight connection of the light sensor with the body part. Thus, apart from the light emitted by the light source and having interacted with the body part, also at least some ambient light ends up in the output signal of the light sensor. This ambient light may impact the measurement signal and make it more difficult or impossible to derive information on a vital sign from the measurement signal.

In order to compensate this effect an ambient light cancellation unit is used in the monitoring device according to the present invention for splitting the output signal into a first signal portion that corresponds to the ambient light component and a second portion that corresponds to the actually desired measurement light component included in the signal. The second signal portion may then actually correspond to the measurement light component itself or to an estimate for it.

However, ambient light also disturbs the output signal generated by the light sensor in a second way. The light emitted by the light source is modulated by the ambient light. Thus, the impact of a given level of light on the output signal of a light sensor may differ for different levels of ambient light. This means that the same measurement light component can lead to different second signal portions depending on the ambient light component. If the second signal portion is to be evaluated in order to obtain a measurement signal (for the further evaluation and derivation of vital sign information therefrom) this effect needs to be compensated. This is particularly important if the transfer function, i.e. the function describing the relation between the input (received light) and output (output signal) of the light sensor, is a non-linear function.

The ambient light modulation removal unit of the present invention compensates this effect. The second signal portion is demodulated by calculating the impact of the ambient light at a specific ambient light level and calibrating the value determined for the second signal portion based on this impact.

Herein, the ambient light component refers to the fraction of light captured by the light sensor that is caused by ambient light sources (i.e. the ambient light level). Ambient light can be caused by daylight or by artificial light sources in the vicinity of the monitoring device. The light sensor will not only capture the desired light but also at least some ambient light. The ambient light level, i.e. the intensity of the ambient light in the vicinity of the living being, impacts the ambient light component (in addition to the shape of the housing of the monitoring device).

The measurement light component refers to the intensity of the captured light resulting from the light emitted by the light source after this emitted light has interacted with the body part. The light sensor receives light and provides an intensity value that describes the sum of the ambient light component and the measurement light component. Consequently, it is usually impossible for the light sensor to distinguish between the two components.

A signal corresponds to a continuous or time-discrete series of values or to one single value (for a specific point in time). The output signal of the light sensor is the analog or digital representation of the measured intensity. Consequently, the output signal includes parts that result from the measurement light component (second signal portion) and parts that result from the ambient light component (first signal portion).

A signal portion corresponds to a fraction of a signal. Usually, a signal portion corresponds to a value describing the intensity of the respective input light. In particular the output signal of the light sensor of the present invention includes two signal portions: a first signal portion representing or corresponding to the ambient light component and a second signal portion representing or corresponding to the measurement light component. The signal portions add up to the output signal.

Separating a signal may particularly refer to dividing the current value of the (digital) signal into a first and a second value. These first and second values are referred to as portions. A signal portion may thus have the same form as the original signal. Each signal portion is indicative of a lower light intensity than the original (output) signal. Demodulating (sometimes also referred to as "modulating") the signal portion corresponds to adjusting the light intensity represented by this signal portion. For this, it may be possible to calculate the measurement signal by means of a calculation that applies a constant or variable factor to the second signal portion or other procedures.

The transfer function is a function that describes a property of the light sensor. Usually, the transfer function will be more or less constant for different light sensors of the same type. The transfer function may be determined during a calibration procedure where predefined input is provided to the light sensor and the output is measured to derive the transfer function or may be obtained from a model of the sensor. The transfer function or its derivative may be stored in the monitoring device.

As used herein, the light sensor may not only refer to the physical sensing component itself (i.e. the actual sensor) but may also include other components such as one or more amplifiers for amplifying a signal that it generated by the physical sensing component based on the received light, filters and/or signal shaping components. The output signal generated by the light sensor is to be understood as the resulting signal being applied to the ambient light cancellation unit. Hence, the transfer function includes all effects on the output signal on its path to the ambient light cancellation unit. Particularly, a non-linear transfer function may be caused by an amplifier for amplifying the signal generated by the physical sensing component rather than by the physical sensing component itself. The device and method disclosed herein compensate for any non-linearity effect in the path up to the ambient light cancellation unit.

The present invention particularly results in the advantage that it becomes possible to better compensate the effect of ambient light on the measurement in comparison to previous approaches. The measurement signal provided by the monitoring device described herein may be used in an apparatus for monitoring vital signs. The vital sign information provided by such an apparatus ma thus also has a higher validity. A device or apparatus according to an aspect of the present invention may be advantageous in applications that require very accurate vital sign information. Also, applications in areas with high levels of ambient lights may be of interest for using the invention.

In a first embodiment the ambient light modulation removal unit is configured to determine a derivative of the transfer function. This derivative may be determined upon request for a specific intensity value of the received light (e.g. the current value of the output signal, the operation point) or for a range (derived function). The derivative may be stored in form of a table or in form of a calculation specification. The advantage is that it becomes possible to better compensate effects on the ambient light level that depend on the gradient of the transfer function.

In a preferred embodiment the ambient light modulation removal unit is configured to demodulate the second signal portion by multiplying it with an inverse of the derivative of the transfer function. Usually, the second signal portion will be represented by a numerical value. This numerical value can be multiplied by an inverse of the derivative of the transfer function at the current operation point. Thereby, different gradients of the transfer function can be compensated. Thus, if the transfer function has a higher gradient in the current working point, i.e. at the level of the current output signal, due to a higher level of ambient light (higher ambient light component), this may be compensated by a multiplication with the inverse of the transfer function. This results in the advantage that it becomes possible to obtain an efficient compensation for the effect of a variation of the ambient light component and its impact on the measurement signal.

In another embodiment the ambient light cancellation unit is configured to determine an estimate for the first signal portion component and subtract said estimate from the output signal to determine the second signal portion. Thus, an estimate for the value of the first signal portion is subtracted, i.e. the value of the output signal is decreased by an estimated value of the first signal portion. This estimate may, e.g., be obtained by determining the output signal at a time, when the light source unit is switched off, i.e. when no measurement light is present (no measurement light component is received). Then the output signal substantially corresponds to the first signal portion. One possible approach for determining an estimate for the first signal portion can be found in WO 2013/0190423 A1 where a circuit is disclosed that provides an estimate for the influence of the ambient light and removes said estimate from the output signal. Removing the estimate of the signal portion corresponding to the ambient light component has the advantage, that the disturbance caused by the ambient light can be efficiently compensated.

In an embodiment the transfer function is a non-linear function. Usually, i.e. for most light sensors, the transfer function is a non-linear function. Such a non-linear function may result in substantial differences of the effect of the measurement light component on the output signal. This means that the second signal portion may be substantially different for the same measurement light components when the ambient light component varies. Then, the compensation provided by the ambient light modulation removal unit of the present invention is even more important.

In another embodiment the above-described monitoring device further comprises a calibration unit for determining the transfer function, wherein the calibration unit is configured to determine a calibration value from the output signal of the light sensor when being exposed to calibration light of predefined intensity. Such a calibration unit may particularly be used in combination with a light emission unit that generates light of a defined light intensity. The light sensor is exposed to this calibration light. The defined light intensity is measured and the output (output signal) of the light sensor for this predefined input is recorded (calibration value or calibration point). This forms the basis for the transfer function. The transfer function may be represented by a lookup table for different single values or ranges. The transfer function may also be represented by an interpolation based on the different measurement points (calibration values) or by a model function adjusted to at least one calibration value. The calibration may be carried out initially prior to using the monitoring device for the first time (i.e. during production of the sensor or monitoring device), on a regular basis or prior to every use. It is usually advantageous to carry out a calibration procedure for every monitoring device as differences in the manufacturing process and/or material tolerances may result in large deviations of the transfer functions.

In a preferred embodiment the calibration unit is configured to apply a curve fitting algorithm to a plurality of calibration values. Preferably, the determined values in the above-outlined calibration procedure are used as input to a curve fitting approach to derive the transfer function. A curve-fitting algorithm allows deriving a continuous function from a plurality of measurement points. Thus, it becomes possible to provide a transfer function that allocates a function value to every possible value of the output signal. Thereby, it is particularly advantageous to use a continuously increasing model function. This may allow avoiding contradictions in the further information processing. Possible curve fitting algorithms include approaches such as least-square fitting and the like.

In an embodiment of the monitoring device as described above, the light source is configured to emit light pulses; and the ambient light cancellation unit is configured to separate the output signal based on the output signal at a point in time when the light source is powered off and based on the output signal at a point in time when the light source emits light. If the light source emits light pulses the difference between the output signal at times when the light source is powered on and at times when the light source is powered off can be exploited. Thus, the ambient light component is measured alone and together with the measurement light component. This corresponds to a time-division multiplexing approach. This configuration represents an efficient approach to determine the impact of the measurement light component. Furthermore, a pulsating light source may be advantageous with regard to the vital sign information extraction.

In a preferred embodiment the monitoring device further includes a filtering unit configured to filter the output signal with a first low-pass filter when the light source emits light to generate a first filtered signal and with a second low-pass filter when the light source is powered off to generate a second filtered signal; and the ambient light cancellation unit is configured to subtract the second filtered signal from the first filtered signal. Thereby, an (analog or digital) signal processing approach to subtract the impact of the ambient light component, i.e. the first signal portion, from the output signal to obtain the second signal portion (or an estimate thereof) becomes possible.

In yet another embodiment the monitoring device further comprises an additional ambient light sensor for receiving ambient light and for generating an ambient light signal; and the ambient light cancellation unit is configured to separate the output signal based on an estimate for the ambient light component derived from the generated ambient light signal. Alternatively or additionally to making use of the above-outlined pulsed light source, it is also possible to use an additional ambient light sensor for obtaining an estimate for the ambient light component alone (without the measurement light component) based on a measurement of the ambient light level. Then, the ambient light signal (corresponding to the ambient light component) can be subtracted from the output signal of the (original) light sensor (corresponding to the ambient light component and the measurement light component) to obtain an estimate for the second signal portion. The advantage of this embodiment is that no pulsed operation of the light source is required.

In a preferred embodiment of the above-outlined monitoring device the light source is configured to emit light of a first wavelength and there is further comprised an additional light source for emitting light of a second wavelength different from the first wavelength. By including two light sources that emit light at different wavelengths it becomes possible to exploit the differences in the absorption characteristics of blood with a different oxygen saturation for light of different wavelengths. This allows obtaining information on the blood oxygen saturation of the patient. Usually, the two light sources will be operated alternatingly, i.e. pulsed in turns. Then, the emitted light can be captured by one light sensor.

In yet another embodiment the light source and the light sensor are configured to be arranged on opposite sides of a body part of the living being; and the measurement light component of the light results from a transmission of the emitted light through said body part. Thereby, a transmissive measurement becomes possible. Light is emitted into a body part and captured on the other side of the body part. Consequently, the light necessarily interacts with the body part (i.e. the tissue and blood therein). A transmissive measurement has the advantage that a robust output signal can be obtained.

In another embodiment the light source and the light sensor are configured to be arranged to face a body part of the living being; and the measurement light component of the light results from a reflection of the emitted light at said body part. Thereby, a reflective measurement becomes possible. Light is emitted into a body part, interacts with the body part and is (partly) reflected. The reflected light is captured by means of the light sensor and evaluated. This is particularly advantageous if a transmissive measurement is not possible, e.g. if a body part is to be examined that is too thick for the emitted light to be transmitted through.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF THE INVENTION

The present invention concerns a monitoring device for providing a measurement signal that carries information on a vital sign of a living being. This measurement signal can be evaluated to derive therefrom vital sign information in a processing unit. This processing unit may be included in the monitoring device or be part of another device. Herein, an apparatus for monitoring refers to an apparatus that includes the monitoring device along with a processing unit for evaluating the measurement signal provided by the monitoring device.

Figure 1:
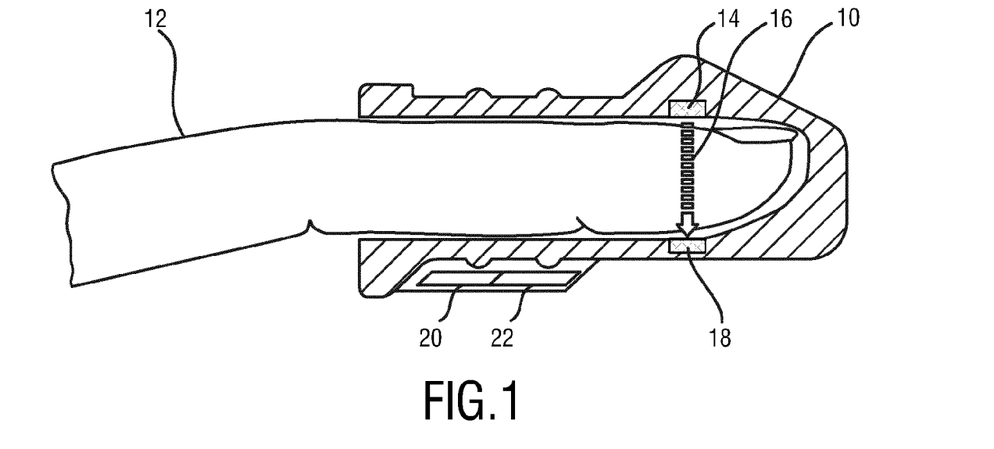
FIG. 1 shows a monitoring device according to an aspect of the present invention.

FIG. 1 illustrates a monitoring device 10 according to an aspect of the present invention in a sectional view. The illustrated device 10 corresponds to a clip that can be applied to a finger 12 of a person. In the following, the present invention is illustrated for the non-limiting example of such a finger clip sensor. Other applications of the present invention are, however, possible, such as in an ear sensor, a body worn sensor or any other wearable (e.g. wristwatch-type device, body belt), etc.

The illustrated device 10 comprises a light source 14 that emits light into a body part 12 of a living being. In the illustrated embodiment the body part corresponds to a finger of a person. The light source 14 usually includes a LED. The emitted light interacts with the finger 12 (or, more precisely, with the tissue and/or blood in the finger). After interacting, the emitted light is captured by means of a light sensor 18. The light sensor 18 (sometimes also referred to as frontend or photosensor) usually includes a photodiode. In addition to the emitted light, the received light 16 also includes ambient light. Herein, the measurement light component describes the portion of the received light that corresponds to the light emitted by the light source 14 that has interacted with the body part 12 and that is received by the light sensor 18. The ambient light component describes the portion of the received light 16 that comes from the ambience.

The light sensor 18 provides an (analog or digital) output signal that can be further processed. The output signal usually corresponds to a reading of the light intensity of the received light 16. The relation of the output signal to the light intensity to which the light sensor is exposed is referred to as transfer function. The transfer function describes a property of the light sensor 18.

In addition to the transmissive measurement as illustrated in FIG. 1 also a reflective measurement principle may be exploited (i.e. the light sensor and the light source are arranged on the same side of the body part and reflected light is captured).

A preferable application area of the monitoring device 10 according to the present invention is blood oxygen saturation monitoring. In this application, the monitoring device 10 usually comprises an additional light source in addition to the light source 14 that emits light of a wavelength different from the light of the light source 14. Usually a red LED and an infrared LED are used. The two LEDs are usually pulsed, i.e. powered on alternatingly, to not interfere with one another. The emitted light in the red and infrared spectrum interacts with blood in the body part 12. After this interaction, the light is captured by the light sensor 18. A change in the blood oxygen saturation results in a change of the color of the blood. Information on this change can be obtained from evaluating the received light, in particular if light of two different wavelengths is used. In addition to the blood oxygen saturation, the heart beat and/or the breathing rate can be derived from the measurement signal.

One problem in this arrangement as already mentioned above is that usually not only the light emitted from the light source is received by the light sensor 18. Depending on the embodiment of the housing of the monitoring device 10, also ambient light is received by the light sensor 18. This ambient light may originate from daylight or from artificial light sources in the vicinity of the person. Usually, different levels of ambient light are present at different times (variations in the ambient light level). Depending on the wavelength of the present ambient light and/or its fluctuations (particularly with respect to fluctuations at a frequency comparable to a heart rate) this ambient light may make it difficult to extract meaningful vital sign information from the measurement signal as the changes in the measurement signal that correspond to the desired vital sign information are usually small.

The light detected by the light sensor 18 thus includes an ambient light component and a measurement light component. Both components end up in the output signal of the light sensor 18.

In order to compensate the influences of ambient light on the measurement signal, the present invention provides an ambient light cancellation unit 20 and an ambient light modulation removal unit 22. The ambient light cancellation unit 20 separates the output signal provided by the light sensor 18 into a first portion that corresponds to the ambient light (ambient light component) and a second portion that corresponds to the light that was originally emitted by the light source 14 (measurement light component). The ambient light modulation removal unit 22 further compensates effects that result from a different sensitivity of the light sensor 18 for different levels of ambient light. The measurement signal generated by the ambient light modulation removal unit 22 thus corresponds to a measure for the measurement light component that is independent of the ambient light component.

Ambient light ends up in the output signal of the light sensor in two ways. On the one hand, it adds up to the output signal if nothing special is done. A higher level of ambient light results in a higher output signal level even if the same amount of light from the light source is captured. On the other hand ambient light modulates the LED light. In other words: the light sensor does not necessarily convert the same amount of (additional) light into the same signal level when being exposed to another level of background or ambient light. Demodulating the signal portion (in the ambient light modulation removal unit 22) corresponds to removing this effect.

The first effect can be compensated by providing an ambient light cancellation unit 20 (may also be referred to as ambient light cancellation circuitry), which removes the contribution of ambient light. The output signal is separated into a first portion corresponding to the ambient light component and a second portion corresponding to the measurement light component. This may, e.g., be done by subtraction as presented in WO 2013/0190423 A1. Therein, a circuit is presented that makes use of the fact that a pulsed light source allows obtaining a measurement of the ambient light component (without the measurement light component) at times when the light source is powered off. The output signal of the light sensor 18 at times when the light source 14 is powered off may then be subtracted from the output signal at times when the light source 14 is powered on to obtain an estimate for the signal portion of the output signal corresponding to the measurement light component (second signal portion).

In other words, ambient light cancellation makes use of the fact that the light of the LED (light source) is pulsed, such that there are time intervals during which only ambient light is present at the light sensor and other time intervals during which the sum of ambient light and light from the light source is present at the light sensor. One possible approach to provide this functionality is to apply different filters, in particular differently configured low-pass filters, to the output signal depending on whether the light source is powered on or not. Therefrom an estimate for the ambient light component and the corresponding signal portion can be obtained.

In other embodiments of the present invention, it may also be possible that an additional light sensor provides a measurement for the ambient light component that can then be used as a basis for removing the ambient light component from the output signal.

Figure 2:
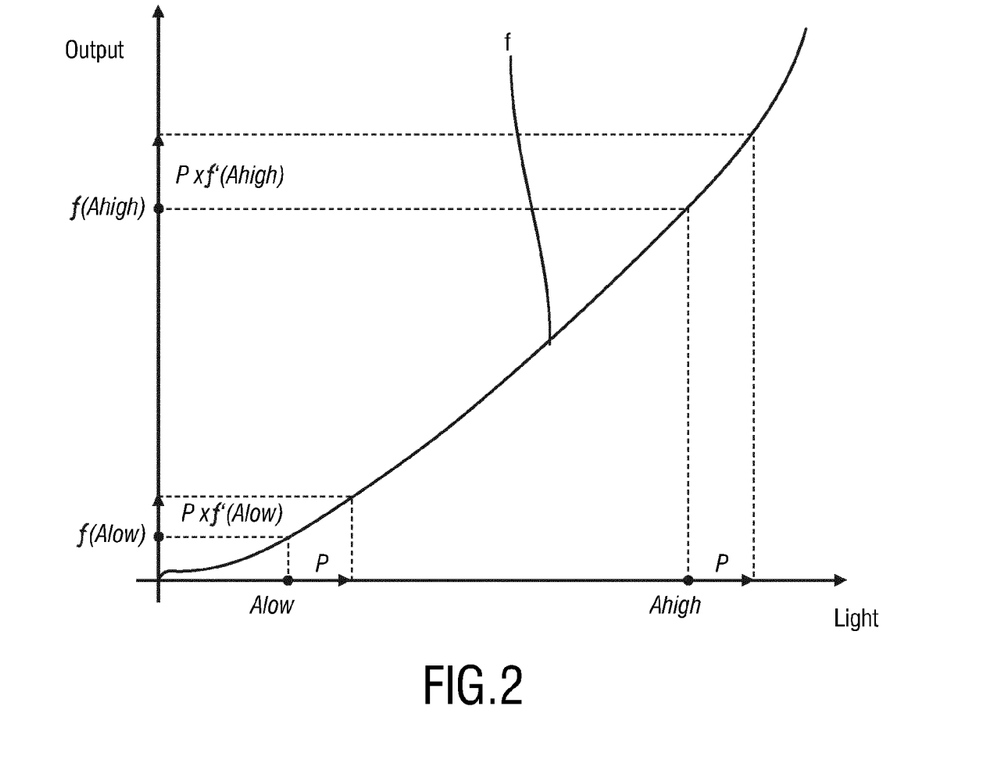
FIG. 2 shows a diagram illustrating the light to output characteristics (transfer function) of a light sensor.

The second effect is further illustrated in FIG. 2. The illustrated transfer function f describes the output characteristics of the light sensor 18. On the x-axis the input light level is illustrated. A light level refers to the light intensity that is present at the light sensor 18. For instance, the light level may correspond to the sum of the ambient light component and the measurement light component. On the y-axis the resulting output signal level is illustrated. This output signal may, e.g., include a first portion corresponding to the ambient light component and a second portion corresponding to the measurement light component. In a time-based view, a fluctuating input generates a fluctuating output. Some fluctuations may, e.g., be attributable to a pulsating light source, other (usually smaller) changes are attributable to a changes in the body part of the living being, such as pulsating blood that results in a varying absorption and that are representative of vital sign information of the living being.

The transfer function f is usually a continuously increasing function. A higher light level yields a higher output signal level. The illustrated non-linear transfer function in FIG. 2 is for illustration purposes and only qualitatively illustrates the relation between the input and output of the light sensor. Other light sensors may have different transfer functions.

As illustrated in FIG. 2, the ambient light may vary between $A_{low}$ and $A_{high}$. Further, due to the pulsating light source, the input light may temporarily be increased by P. Thus, A represents the ambient light component and P represents the measurement light component. The output signal of the light sensor then varies between $f(A_{low})$ and $f(A_{high})$ when the LED is off and between $f(A_{low})+P\cdot f'(A_{low})$ and $f(A_{high})+P\cdot f'(A_{high})$ when the LED is powered on. f(A) represents the signal portion of the output signal corresponding to the ambient light component in the first case (first signal portion). The function f' is the derivative of the transfer function f.

If the signal portion corresponding to the ambient light component is removed from the output signal (in the ambient light cancellation unit), the output thus varies between $P\cdot f'(A_{low})$ and $P\cdot f'(A_{high})$. Thus, if the transfer function f is non-linear (which is usually the case), the output of the ambient light cancellation unit, i.e. the second signal portion, still depends on the ambient light component. This is referred to as ambient light modulation herein. The ambient light modulation removal unit seeks to compensate this ambient light modulation.

The ambient light modulation can be defined as the peak-to-peak output variation divided by the average output signal level:

$$\frac{P\cdot [f'(A_{high}) - f'(A_{low})]}{P\cdot [f'(A_{high}) + f'(A_{low})]/2} = \frac{f'(A_{high}) - f'(A_{low})}{[f'(A_{high}) + f'(A_{low})]/2}$$

This relation is a measure for the linearity of the transfer function f. If the derivative of the transfer function f was linear then f' is independent of the ambient light component. Then, the ambient light modulation is 0. Further, the relation also represents a lower bound for the ambient modulation. The outcome of the relation depends on variations in f' (i.e. the non-linearity of f), $A_{low}$ and $A_{high}$ (larger ranges generally cause variations of f to be larger) and on P (larger values generally cause non-linearity effects to smooth out, while smaller values of P make non-linearity effects more pronounced). Thereby, P follows from the power of the light source. A decreasing power causes non-linearity effects to be more pronounced. Usually, an overall ambient light cancellation ≤60 dB is required.

Thus, ambient light modulation removal is of particular importance if the monitoring device is exposed to comparably high ambient light ranges (large variations). Then, the influence of the light to output characteristic (transfer function) of the light sensor can become dominant.

Figure 3:
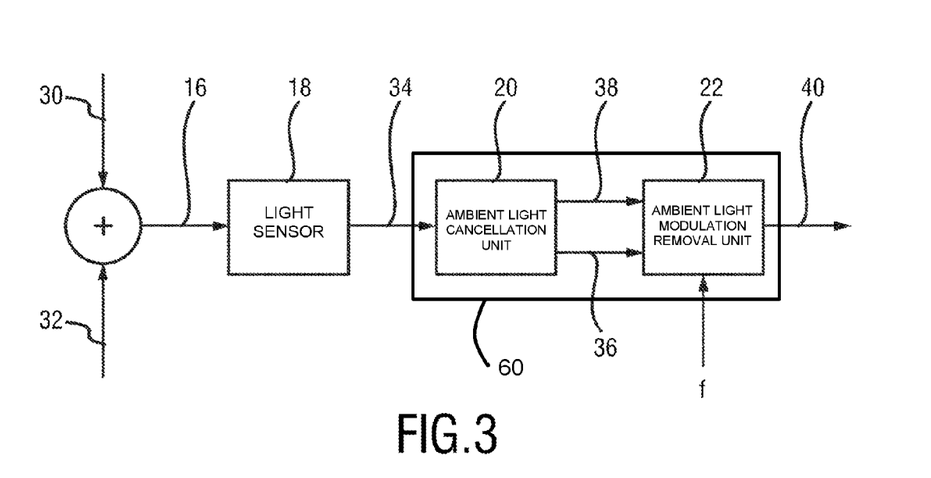
FIG. 3 schematically illustrates the signal processing approach according to the present invention.

The present invention allows compensating this effect by means of the ambient light modulation removal unit 22. FIG. 3 illustrates the data processing in an embodiment of the present invention. An ambient light component 30 and an measurement light component 32 (which corresponds to the light emitted by the light source) combine to the light 16 being received in the light sensor 18 (may also be referred to as frontend). The light sensor 18 provides an output signal 34 to the ambient light cancellation unit 20. This output signal 34 includes a first signal portion, i.e. a first part that corresponds to the ambient light component 30 and a second signal portion, i.e. a second part that corresponds to the measurement light component 32. The ambient light cancellation unit 20 separates the two signal portions. Thus, a first output of the ambient light cancellation unit 20 corresponds to the first signal portion 36 (that represents the influence of the ambient light) and a second output corresponds to the second signal portion 38 (that represents the modulated light of the light source after interaction with the body part of the living being). Based on the transfer function f and on the first signal portion 36, the ambient light modulation removal unit 22 compensates the effect of a variation of the ambient light component 30 and generates a measurement signal 40 (i.e. demodulates the second signal portion). This measurement signal 40 is thus directly representative of the measurement light component 32 independent of the currently present ambient light component 30 and can be used as a basis for the extraction of vital sign information of the living being.

In other words, the output of the ambient light cancellation unit 20, i.e. the first signal portion 36 corresponding to the ambient light component 30 and the second signal portion 38 corresponding to the modulated light of the light source, is processed based on the inverse of the derivative f' of the transfer function f in the working point (which is defined by the ambient light component A). The measurement signal 40 corresponds to the second signal portion 38 divided by f'(A). As the second signal portion 38 corresponds to the measurement light component $P\cdot f'(A)$ this can be reduced to P, which corresponds to the actual measurement light component 32. Thus, the effect of the variation of the ambient light component A is removed and a measurement signal being representative of P is provided.

The therefor required transfer function f (which is required to calculate the derivative f') is usually determined in a calibration procedure. Such a calibration procedure may be carried out by a calibration unit in the device 10. Preferably, the calibration procedure is carried out at production time of the device 10. Usually, an artificial light source is configured to provide light at various intensities (calibration light). The output signal of the light sensor is measured and at least one calibration value is calculated. A calibration value thus corresponds to a value pair calibration light (light intensity) and corresponding output signal. The curve f is derived from at least one calibration value by means of a model or from multiple calibration values by means of a curve fitting algorithm. Then, f' is derived from f by differentiation and stored in the device 10 in some form (e.g. a formula or table) such that it can be applied to different levels of A in order to perform the above-outlined processing. If, e.g., a polynomial curve fit on f is done a symbolic/analytic differentiation may be performed and the coefficients from the fitted function may be filled into the formula for the derivative f' (e.g. $f=a\cdot x^2$, $f'=2\cdot a\cdot x$, i.e. the function f is fitted from which follows coefficient a, from which follows f).

Figure 4:
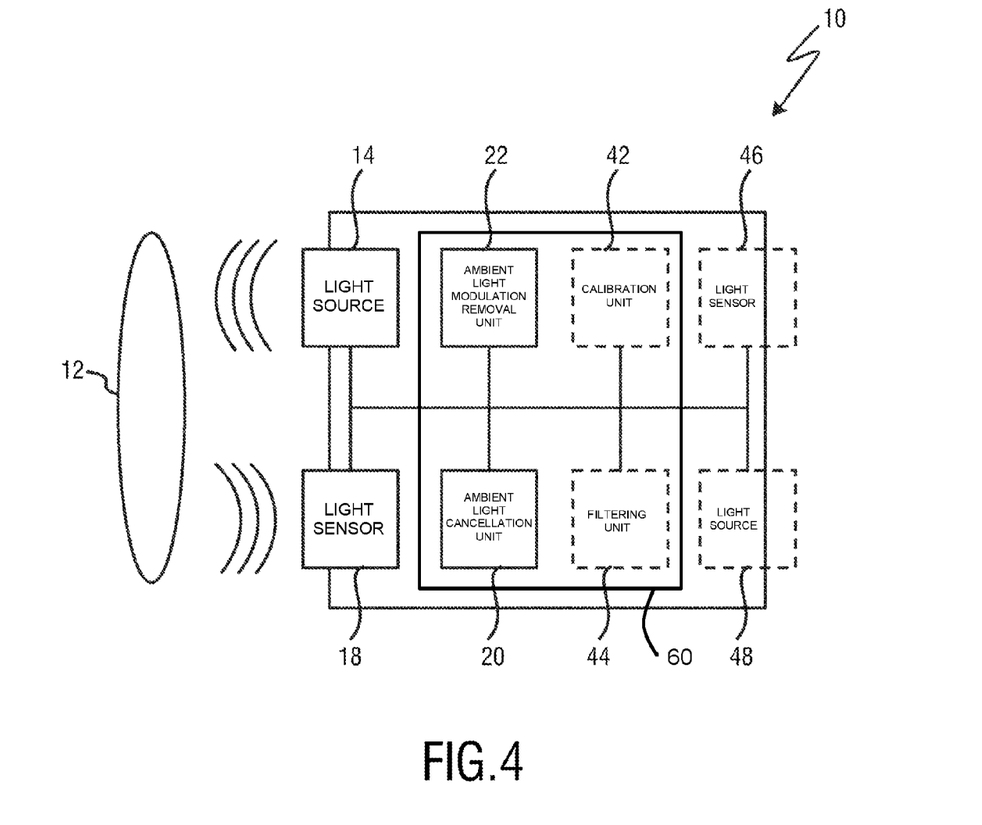
FIG. 4 schematically illustrates another embodiment of a monitoring device according to the present invention.

FIG. 4 schematically illustrates further embodiments of devices according to the present invention. Therein, the dashed lines represent optional components that may or may not be comprised in the monitoring device or in the apparatus for monitoring a vital sign of a living being according to the present invention.

Apart from the light source 14 (that emits light into a body part 12 of a living being), the light sensor 18, the ambient light cancellation unit 20 and the ambient light modulation removal unit 22, there may further be comprised a calibration unit 42. This calibration unit 42 performs the above-outlined calibration procedure.

Still further, the may be comprised a filtering unit 44. Such a filtering unit 44 may particularly be configured to filter the output signal by means of different filtering approaches depending on whether or not the light source 18 emits light. In a preferable embodiment, the light source 14 is configured to emit pulsed light, i.e. to periodically emit light in the form of pulses. A time period in which the light is emitted is followed by a time period in which no light is emitted. This is, however, not required in all embodiments of the present invention. The filtering unit 44 particularly allows carrying out the ambient light cancellation procedure presented in WO 2013/190423 A1 as briefly outlined above.

Further, there may be comprised an additional light sensor 46, which allows capturing the ambient light component alone (without the measurement light component). Such an additional light sensor 46 will usually be arranged spatially separated from the light sensor 18 such that it allows capturing ambient light in order to obtain an estimate for the ambient light component present at the light sensor 18 without being disturbed by the measurement light component. This additional light sensor 46 preferably includes a photodiode.

Still further, the device 10 may also comprise an additional light source 48. This additional light source 48 may particularly include a LED that emits light of a different wavelength than the original light source 14. In a preferred embodiment, the light source 14 emits red light and the additional light source 48 emits infrared light (i.e. includes an infrared LED). Thereby, it becomes possible to carry out a measurement of the blood oxygen saturation of the living being by evaluating absorption characteristics of light of different wavelengths in the blood.

Figure 5:
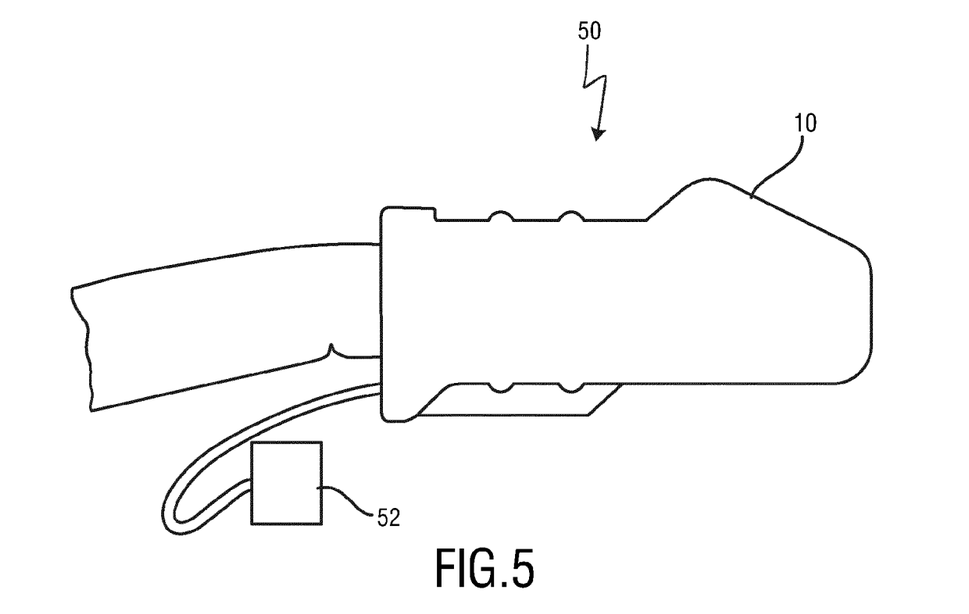
FIG. 5 shows an apparatus for monitoring a vital sign of a living being according to an aspect of the present invention.

In yet another aspect of the present invention as illustrated in FIG. 5 there is presented an apparatus 50 for monitoring a vital sign of the living being. This apparatus 50 includes the monitoring device 10 along with a processing unit 52 (may also be referred to as processor) to extract vital sign information from the measurement signal provided by the monitoring device. The processing unit 52 extracts vital sign information of the living being from the measurement signal. For this, preferably remote photoplethysmography is used. The extracted vital sign information particularly includes at least one of the blood oxygen saturation, the heart rate and the breathing rate of the living being.

In the illustrated embodiment in FIG. 5 the processing unit is spatially separated from the monitoring device 10. In other embodiments, it may, however, also be possible, that the processing unit 52 is actually integrated into the device 10.

The derived vital sign information may be provided to the user or to a physician by means of a human machine interface. For this, a wireless or wired interface may be provided in the apparatus 50. Alternatively or additionally, the vital sign information may be directly communicated to a database and/or internet based storage.

Figure 6:
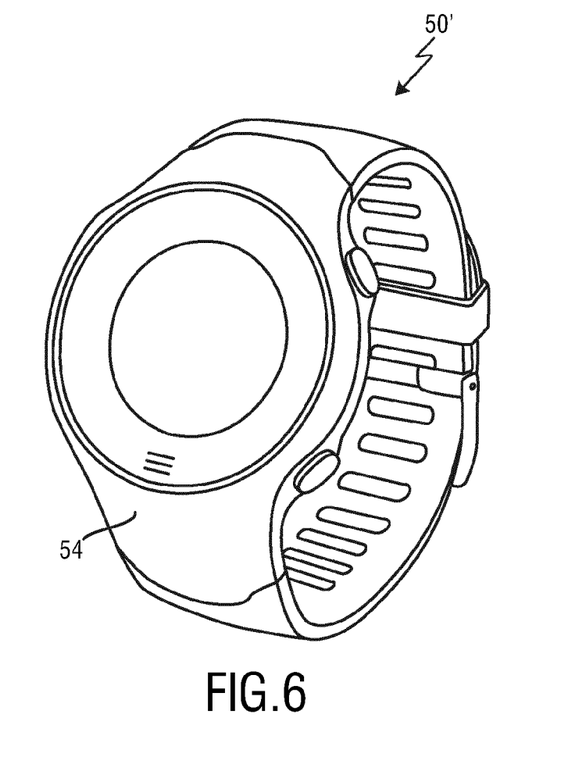
FIG. 6 shows another embodiment of an apparatus for monitoring a vital sign of a living being according to an aspect of the present invention.

FIG. 6 shows another preferred embodiment of an apparatus 50' according to an aspect of the present invention. According to this embodiment the monitoring device and the processing unit as described above are integrated into a wristwatch 54. Preferably, the apparatus according to the present invention may be embodied as a wrist worn heart rate sensor that uses green light (e.g. MIO Alpha, Adidas MiCoach, etc.). The wristwatch 54 is similar to a normal watch and can be worn on a daily basis. In this wristwatch 5, the light source and light sensor may particularly be integrated in the backside of the watch to face the skin of the person wearing the wristwatch 54. The processing unit may be integrated in the housing of the watch.

Such a wristwatch 54 may be worn in fitness and lifestyle application areas and also in medical application areas. The wristwatch 54 may also comprise additional sensors (e.g. motion sensors, ambient sensors, etc.), a display for displaying information to the user and/or other interface components (acoustic, haptic, etc.) and may provide an alarm function based on the monitored vital sign of the living being.

In other embodiments of the present invention the ambient light cancellation unit, the ambient light modulation removal unit, the processing unit, the calibration unit and the filtering unit may partly or entirely be included in on or more microprocessor devices (e.g. IC, ASIC, FPGA, etc.), as shown, for example, by microprocessors 60 in FIGS. 3 and 4. It may be possible that some or all of the functionalities of the units are implemented in hard- and/or in software. Multiple units may be combined into one unit. It is also possible that some of the functions are carried out in one or more units that are actually spatially separated from the monitoring device and connected thereto by means of a wired or wireless interface.

Figure 7:
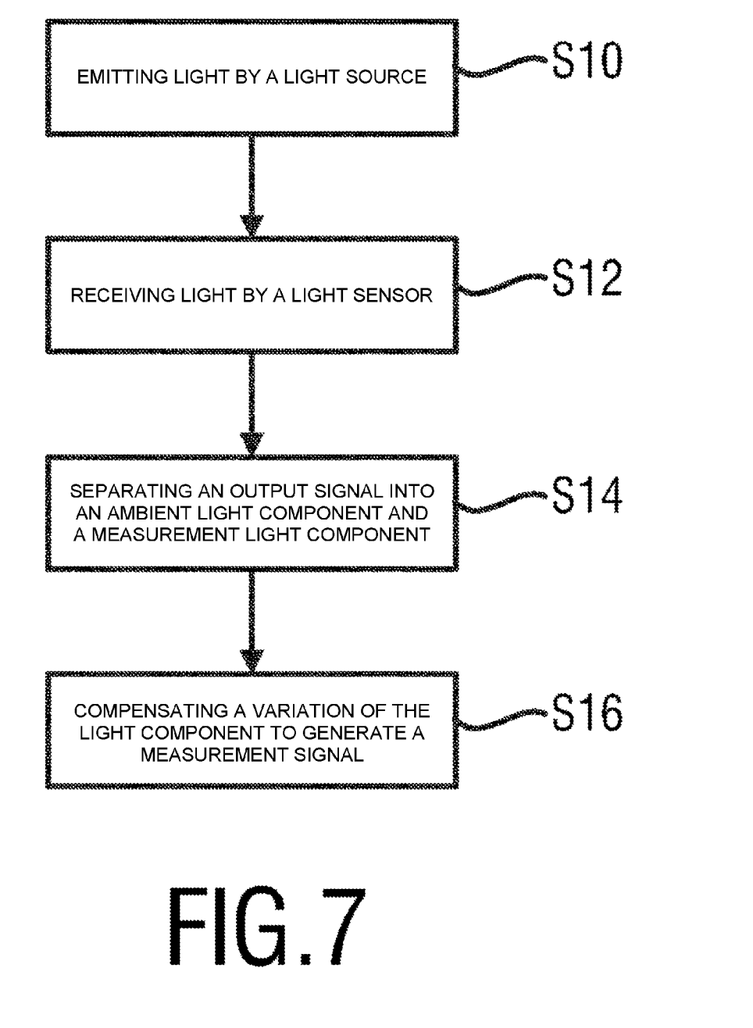
FIG. 7 schematically illustrates a monitoring method according to an aspect of the present invention.

In FIG. 7 a method according to an aspect of the present invention is schematically illustrated. The method comprises the steps of emitting light (step S10) by means of a light source such as a LED. The emitted light is received (step S12) by a light sensor such as a photodiode. This photodiode provides an output signal which is then separated (step S14) into a first signal portion corresponding to an ambient light component and a second signal portion corresponding to a measurement light component. Then, the effect of a variation in the ambient light component is compensated (step S16) to generate a measurement signal.

Embodiments of the present invention can be used in the context of medical vital sign monitoring for babies, infants and adults (e.g. in a hospital environment) but also in fitness and lifestyle applications or even for other living beings such as animals. Vital sign information that can be extracted from the measurement signal particularly corresponds to a heart rate, a breathing rate or blood oxygen saturation of a person.

Apart from the illustrated finger clip, embodiments of the present invention may also be in the form of different other clips to be attached to other body parts (ear or ear lobe, toe, etc.) or in the form of pads. The present invention may even be applied remote monitoring devices for remotely measuring light reflected from or transmitted through a body part for deriving PPG signals (e.g. by use of a camera) by a commonly known technology called remote photoplethysmography, which does not require physical contact with the body part of the living being.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A monitoring device comprising:
   a light source configured to emit light into a body part of a living being;
   a light sensor configured to receive light including an ambient light component and a measurement light component resulting from interactions of said emitted light with said body part and configured to generate an output signal, wherein a transfer function describes the relation between the output signal and the received light; and
   a microprocessor device comprising:
      an ambient light cancellation unit configured to separate the output signal into a first signal portion corresponding to the ambient light component and a second signal portion corresponding to the measurement light component;
      an ambient light modulation removal unit configured to compensate a variation of the ambient light component by demodulating the second signal portion based on the transfer function and the first signal portion to generate a measurement signal; and
      a processing unit configured to derive and monitor information on a vital sign of the living being from the measurement signal.

2. The monitoring device of claim 1, wherein the ambient light modulation removal unit is configured to determine a derivative of the transfer function.

3. The monitoring device of claim 2, wherein the ambient light modulation removal unit is configured to demodulate the second signal portion by multiplying it with an inverse of the derivative of the transfer function.

4. The monitoring device of claim 1, wherein the ambient light cancellation unit is configured to determine an estimate for the first signal portion component and subtract said estimate from the output signal to determine the second signal portion.

5. The monitoring device of claim 1, further comprising a calibration unit configured to determine the transfer function, wherein the calibration unit is configured to determine a calibration value from the output signal of the light sensor when being exposed to calibration light of predefined intensity.

6. The monitoring device of claim 5, wherein the calibration unit is configured to apply a curve fitting algorithm to a plurality of calibration values.

7. The monitoring device of claim 1,
   wherein the light source is configured to emit light pulses; and
   wherein the ambient light cancellation unit is configured to separate the output signal based on the output signal at a point in time when the light source is powered off and based on the output signal at a point in time when the light source emits light.

8. The monitoring device of claim 7,
   further including a filtering unit configured to filter the output signal with a first low-pass filter when the light source emits light to generate a first filtered signal and with a second low-pass filter when the light source is powered off to generate a second filtered signal;
   wherein the ambient light cancellation unit is configured to subtract the second filtered signal from the first filtered signal.

9. The monitoring device of claim 1,
   further comprising an additional ambient light sensor configured to receive ambient light and for generating an ambient light signal;
   wherein the ambient light cancellation unit is configured to separate the output signal based on an estimate for the ambient light component derived from the generated ambient light signal.

10. The monitoring device of claim 1, wherein the light source is configured to emit light of a first wavelength, further comprising an additional light source configured to emit light of a second wavelength different from the first wavelength.

11. The monitoring device of claim 1,
    wherein the light source and the light sensor are configured to be arranged on opposite sides of the body part of the living being; and
    wherein the measurement light component of the light results from a transmission of the emitted light through said body part.

12. The monitoring device of claim 1,
    wherein the light source and the light sensor are configured to be arranged to face a body part of the living being; and
    wherein the measurement light component of the light results from a reflection of the emitted light at said body part.

13. A monitoring method comprising the steps of:
    emitting light into a body part of a living being;
    receiving light including an ambient light component and a measurement light component resulting from interactions of said emitted light with said body part and for generating an output signal, wherein a transfer function describes the relation between the output signal and the received light;
    separating the output signal into a first signal portion corresponding to the ambient light component and a second signal portion corresponding to the measurement light component;
    compensating a variation of the ambient light component by demodulating the second signal portion based on the transfer function and the first signal portion to generate a measurement signal; and
    deriving and monitoring information on a vital sign of the living being from the measurement signal.

14. The monitoring method of claim 13, wherein the transfer function is a non-linear function.

15. The monitoring method of claim 13, further comprising the step of determining a calibration value from the output signal of the light sensor when being exposed to calibration light of predefined intensity.

* * * * *